United States Patent
Zeyher

(10) Patent No.: US 10,744,252 B2
(45) Date of Patent: Aug. 18, 2020

(54) PERITONEAL DIALYSIS MACHINE HAVING A TORQUE LIMITING DEVICE

(71) Applicant: FRESENIUS MEDICAL CARE DEUTSCHLAND GMBH, Bad Homburg (DE)

(72) Inventor: Peter Zeyher, Darmstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 255 days.

(21) Appl. No.: 15/752,127

(22) PCT Filed: Aug. 10, 2016

(86) PCT No.: PCT/EP2016/001381
§ 371 (c)(1),
(2) Date: Feb. 12, 2018

(87) PCT Pub. No.: WO2017/025198
PCT Pub. Date: Feb. 16, 2017

(65) Prior Publication Data
US 2018/0236154 A1    Aug. 23, 2018

(30) Foreign Application Priority Data

Aug. 11, 2015    (DE) .......................... 10 2015 010 418

(51) Int. Cl.
*A61M 1/16*    (2006.01)
*A61M 1/28*    (2006.01)
(Continued)

(52) U.S. Cl.
CPC ............ *A61M 1/1643* (2014.02); *A61M 1/28* (2013.01); *G01G 17/04* (2013.01); *G01G 21/22* (2013.01);
(Continued)

(58) Field of Classification Search
CPC .................. A61M 1/643; A61M 1/28; A61M 2205/3379; A61M 2205/3393; G01G 17/04; G01G 21/22; G01G 23/005
See application file for complete search history.

(56) References Cited

U.S. PATENT DOCUMENTS 4,338,825 A * 7/1982 Amlani ................ G01G 3/1412
177/156
4,467,661 A * 8/1984 Somal ...................... G01G 3/12
177/229
(Continued)

FOREIGN PATENT DOCUMENTS

| DE | 9406898 | 1/1995 |
|---|---|---|
| DE | 60029744 | 8/2007 |
| DE | 112010003845 | 4/2015 |

*Primary Examiner* — Randy W Gibson
(74) *Attorney, Agent, or Firm* — Jacobson Holman, PLLC.

(57) ABSTRACT

A peritoneal dialysis machine is provided having a machine housing and a weighing pan for receiving one or more solution bags. The weighing pan is connected to a weighing cell for weight measurement, wherein one or more torque limiting devices are provided which prevent the occurrence of a torque or of a torque exceeding a limit value in the weighing cell. The torque limiting device is configured such that with a torque acting on the weighing pan, it moves the weighing pan such that it comes into contact with the machine housing or with an element connected to the machine housing such that the torque is led off into the machine housing or into the element.

14 Claims, 3 Drawing Sheets

(51) Int. Cl.
  *G01G 17/04*   (2006.01)
  *G01G 21/22*   (2006.01)
  *G01G 23/00*   (2006.01)

(52) U.S. Cl.
  CPC ... *G01G 23/005* (2013.01); *A61M 2205/3379* (2013.01); *A61M 2205/3393* (2013.01)

(56) References Cited

U.S. PATENT DOCUMENTS

| | | | |
|---|---|---|---|
| 4,479,561 A | 10/1984 | Feinland et al. | |
| 4,540,057 A * | 9/1985 | Freeman | G01G 3/1414 177/154 |
| 4,726,435 A * | 2/1988 | Kitagawa | G01G 23/06 177/154 |
| 5,048,624 A * | 9/1991 | Pike | G01G 7/06 177/154 |
| 5,096,007 A * | 3/1992 | Burkhard | G01G 23/005 177/187 |
| 5,319,161 A * | 6/1994 | Miller | G01G 23/005 177/154 |
| 5,373,116 A * | 12/1994 | Schneider | G01G 23/005 177/154 |
| 5,521,334 A * | 5/1996 | Freeman | G01G 23/005 177/154 |
| 5,604,334 A | 2/1997 | Lüchinger et al. | |
| 5,773,729 A * | 6/1998 | Nahar | G01G 23/005 73/862.382 |
| 5,923,000 A * | 7/1999 | Tschopp | G01G 23/005 177/154 |
| 6,354,159 B2 * | 3/2002 | Burkhard | G01G 23/005 73/862.53 |
| 6,958,453 B2 * | 10/2005 | Burkhard | G01G 23/005 177/184 |
| 2005/0045388 A1 | 3/2005 | Burkhard | |
| 2006/0289207 A1 | 12/2006 | Burkhard et al. | |
| 2011/0160649 A1 | 6/2011 | Pan | |
| 2018/0236153 A1 * | 8/2018 | Zeyher | A61M 1/28 |

* cited by examiner

PERITONEAL DIALYSIS MACHINE HAVING A TORQUE LIMITING DEVICE

BACKGROUND OF THE INVENTION

1. Field of the Invention

The present invention relates to a peritoneal dialysis machine having at least one machine housing and having at least one weighing pan for receiving one or more solution bags, wherein the weighing pan is connected to at least one weighing cell for weight measurement.

2. Description of the Related Art

In peritoneal dialysis machines known from the prior art, a pan is located above the machine housing which serves to receive a bag which is filled with dialyzate which is delivered to the patient. This pan—also called a weighing pan in the following—is connected via a connection mechanism such as a rod to a weighing cell which is located in or at the machine housing. The weighing cell determines the weight of the weighing pan or of the bag located therein.

On an improper actuation, overload or uneven load distribution on the weighing pan, the case can occur that the weighing cell is overloaded and may be damaged in so doing.

SUMMARY OF THE INVENTION

It is therefore the underlying object of the present invention to further develop a peritoneal dialysis machine of the initially named kind such that an overload of the weighing cell is reliably prevented in a comparatively simple manner.

This object is achieved by a peritoneal dialysis machine of the initially named kind in that one or more torque limiting devices are provided which prevent the occurrence of a torque or of a torque exceeding a limit value in the weighing cell, with the torque limiting device being configured such that, with a torque acting on the weighing pan, it moves the weighing pan such that it comes into contact with the machine housing or with at least one element connected to the machine housing such that the torque is led off into the machine housing or into the element.

It is thus the underlying idea of the present invention to effect a protection of the weighing cell of the peritoneal dialysis machine in that on an occurrence or an exceeding of a certain torque, forces are led off from the weighing pan into the machine housing or into an element directly or indirectly connected thereto so that no action takes place on the weighing cell by forces or torques or no forces or torques exceeding the permitted action on the weighing cell act thereon.

The element can be any desired element of the peritoneal dialysis machine. It is preferably an element located at the upper side of the machine housing.

The movement of the weighing pan can take place, for example, upwardly or downwardly or also in a lateral direction. It is important that the weighing pan comes into mechanical contact with the machine housing or with the named element at or from a certain torque onward and is thus so-to-say supported at the machine housing or at the element and preferably at the upper housing side. Further forces or torques are then led off through the machine housing or through the element and do not have to be taken up by the weighing cell which is protected accordingly.

Provision is preferably made that the torque limiting device is configured such that it only moves the weighing pan at a torque acting on the weighing pan and exceeding a limit value such that it comes into contact with the machine housing or with an element connected to the machine housing such that the torque is led off into the machine housing or into the element. The contact between the weighing pan and the machine housing/element thus preferably does not occur at any occurring torque, but rather only when the torque exceeds a limit value.

Provision is made in an embodiment of the invention that the torque limiting device has at least one first element and at least one second element, wherein the first element is formed by at least one body which has at least one recess from which at least one slanted surface extends in a manner slanted with respect to the horizontal and with respect to the vertical. The at least one second element is received in the recess and is rotatable relative to the first element. If a rotation of the two elements with respect to one another takes place, the second element moves along the slanted surface, which has the consequence that the weighing pan is moved to or away from the machine housing.

The relative movement or relative rotation of the two elements with respect to one another can occur, for example, if an attempt is made to rotate the peritoneal dialysis machine using the weighing pan. If the first element is arranged indirectly or directly at the weighing pan and if the second element is arranged indirectly or directly at the machine housing, a relative rotation of the two elements then occurs with respect to one another, which results in an intervention of the torque limiting device. In this case, from a specific torque onward, the weighing pan enters into contact with e.g. the upper side of the machine housing so that the forces and torques acting on the weighing pan are led off into the machine housing.

Provision is preferably made that the recess has at least two of the inclined surfaces which run toward one another.

In the plan view of the first element, the slanted surfaces of the first element can form the sides of a triangle whose one side is open so that the second element can be received in the recess. The open side can, for example, be the upwardly disposed side or the downwardly disposed side of the triangle.

Any other desired geometrical shapes are also covered by the invention in place of a triangle.

The second element, which is moved along the at least one slanted surface, can be designed as a bar-shaped part, for example.

The first or second element can be arranged rotationally fixed relative to the weighing pan and the other element can be arranged rotationally fixed relative to the machine housing.

The first or second element can be arranged directly at the weighing pan or directly at the machine housing or can also only be indirectly connected to the weighing pan or to the machine housing.

It is conceivable that the weighing pan is arranged at a fastening rod whose other end is connected to the weighing cell.

The torque limiting device can be configured such that it limits the torque or fully prevents the effect of a torque on the weighing cell which arises on rotating the weighing pan about its fastening rod, with provision preferably being made that the fastening rod extends vertically. A slanted arrangement of the fastening rod is, however, also covered by the invention.

In a further embodiment of the invention, the torque limiting device has at least one torsion spring.

The torsion spring can be of plate shape.

It preferably serves to keep a torque or an excessive torque away from the weighing cell which arises due to a tilt movement or tilt load of the weighing pan. This is the case when the weighing pan is unevenly loaded relative to its fastening point at which the fastening rod or another fastening element engages.

The torsion spring can have a first section which is connected to an element of the weighing pan. The first section is subjected to torsion on a tilt movement of the weighing pan.

The first section can be arranged at the center of the torsion spring and can be surrounded over its full periphery or partly by a second section which is not subjected to torsion or is subjected to less torsion on the tilt movement than the first section.

In a conceivable embodiment of the invention, the torsion spring is arranged at the lower side of the weighing pan.

As stated, the torque limiting device can be configured such that it limits or prevents a torque which acts on the weighing cell and which arises on a tilt load or a tilt movement of the weighing pan about e.g. a horizontal axis.

The torque limiting device can be configured such that it limits the torque acting on the weighing cell or prevents the action of a torque on the weighing cell which arises on a tilt loading of the weighing pan about a tilt axis which extends e.g. perpendicular to the longitudinal axis of the weighing pan. If the weighing pan has an elongate shape, the longitudinal axis extends in the longitudinal direction of the weighing pan and the tilt axis at an angle thereto, preferably perpendicular thereto.

The weighing pan can be a heated pan so that the weighing pan is configured as a heating pan in which one or more solution bags are heated.

A plurality of solution bags containing fresh dialyzate can be arranged in the weighing pan. It is in particular conceivable to dispense with a heating bag such as is known from known peritoneal dialysis machines and instead to arrange a plurality of solution bags containing the dialyzate in the weighing pan.

With known peritoneal dialysis machines, a heating bag is located in the weighing pan which is connected via hose lines to solution bags containing the dialyzate. The dialyzate moves from the solution bags into the heating bag, is heated therein and then moves to the patient.

In a preferred embodiment of the invention, such a separate heating bag is dispensed with, i.e. the hose set does not have any heating bag. All the solution bags or a plurality of solution bags required for a treatment are rather simultaneously located in the weighing pan and are heated therein. Care must in particular be taken on such a comparatively high load of the heating pan that no damage occurs to the weighing cell.

It is pointed out at this point that the bag covers any desired reception container which is suitable for receiving a solution. This container can have rigid or also flexible walls. It is furthermore pointed out that the term "pan" is not limited to a pan shape in a narrower sense, but rather also covers any desired receiver.

BRIEF DESCRIPTION OF THE DRAWINGS

Further details and advantages of the present invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
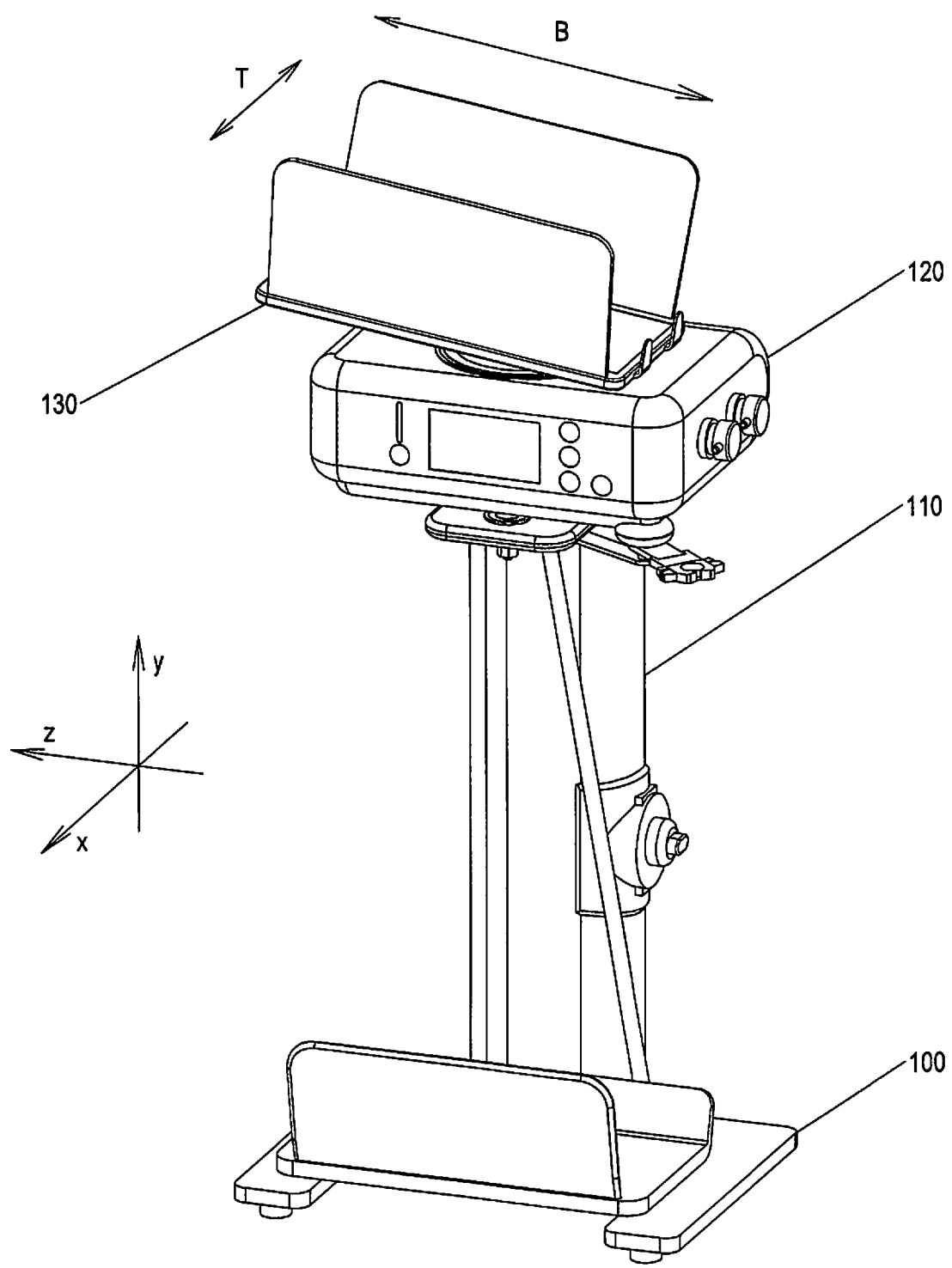
FIG. 1: a perspective view of a peritoneal dialysis machine in accordance with the invention.

A peritoneal dialysis machine in accordance with the invention can be seen from FIG. 1.

It has a machine stand 100, a housing carrier 110 extending upwardly from this and a machine housing 120 which is arranged at the housing carrier 110. The control required for the operation of the machine and optionally display and/or operating elements are located in the machine housing 120.

The weighing pan 130 is located above the machine housing 120; the weighing pan is heatable and will therefore be called a heating pan 130 in the following. The heating pan 130 has a width B and a depth T, with the width B being larger than the depth T.

Figure 2:
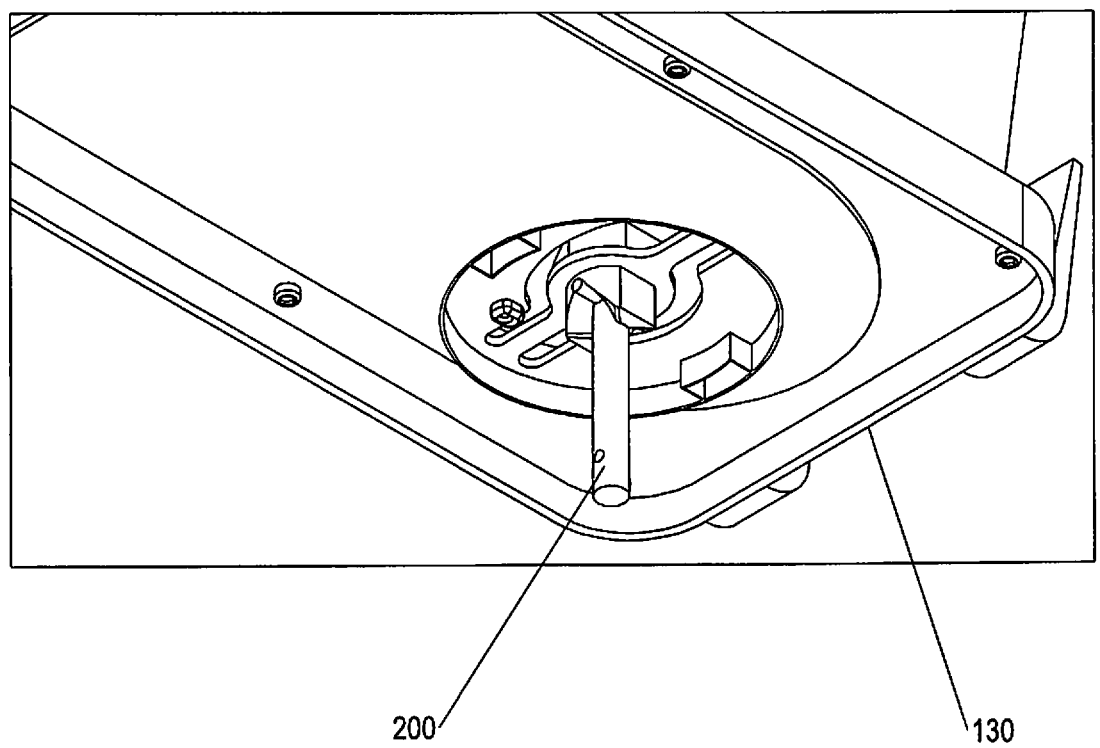
FIG. 2: a perspective view of the weighing pan from below.

The heating pan 130 is connected via a fastening rod 200 to a weighing cell arranged in the machine housing 120, with the fastening rod 200 being visible, for example, from FIG. 2. The fastening rod 200 is arranged vertically.

In accordance with the coordinate system shown in FIG. 1, the x axis extends in the depth direction of the heating pan 130, the z axis extends in the width direction of the heating pan 130 and the y axis extends in the direction of the fastening rod 200, i.e. vertically upwardly.

The peritoneal dialysis machine in accordance with the present invention has two torque limiting devices which have the object of keeping torques which are too large or of keeping any torque at all away from the weighing cell and of protecting the weighing cell in this manner.

FIG. 2 shows the heating pan 130 from below in a perspective view. The fastening rod 200 which supports the heating pan 130 and conducts its weight onto the weighing cell, not shown, extends downwardly from the heating pan 130.

Figure 3:
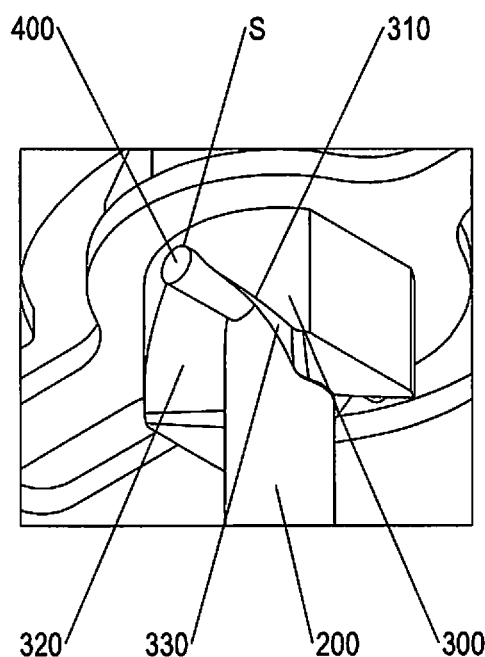
FIG. 3: an enlarged perspective view of the weighing pan from below in the region of the torque limiting device without a torque action.
Figure 4:
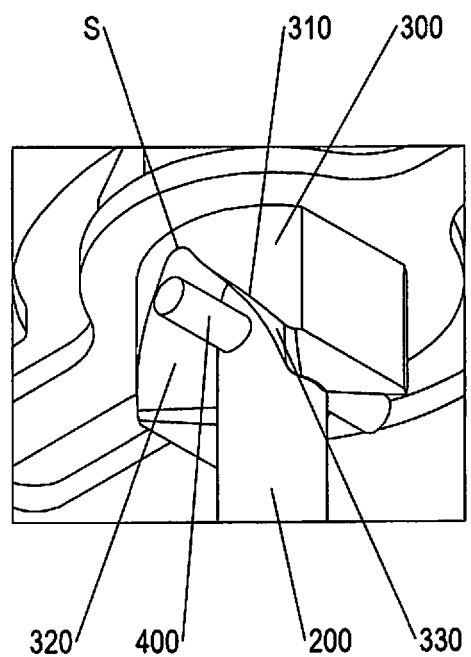
FIG. 4: an enlarged perspective view of the weighing pan from below in the region of the torque limiting device with a torque action.

Two torque limiting devices, of which the first one is shown enlarged in FIG. 3 and in FIG. 4, are located at the bottom at the heating pan.

The first torque limiting device comprises a first element in the form of the body 300. The body 300 has a substantially cylindrical design. It is fixedly connected to the lower side of the heating pan so that a movement of the heating pan produces a corresponding movement of the body.

A V-shaped incision or a V-shaped recess 310, whose tip S faces upwardly and whose lower side is open, is located at the lower side of the body 300.

The free surfaces of the recess 310 are marked by reference numerals 320 and 330 in FIG. 2. These surfaces 320, 330 can be planar or curved.

The second element is located in the form of the rod 400 at the fastening rod 200 and extends in a direction perpendicular to or also slanted with respect to the longitudinal direction of the fastening rod 200. The rod 400 is arranged fixedly at the fastening rod 200. The body 300 is rotatable relative to the fastening rod 200.

As can be seen from FIG. 3, the rod 400 is located at the highest point, i.e. at the tip S of the recess 300, when no torque acts on the heating pan 130.

The fastening rod 200 is rotationally fixedly arranged at the machine housing 120 or at the weighing cell arranged therein. A torque acting on the fastening rod about the longitudinal axis of the fastening rod would thus be transmitted to the weighing cell.

The rod 400 is arranged rotationally fixedly at the fastening rod 200.

If now a torque acts on the heating pan 130, for example because a user turns it, this torque is not transmitted to the fastening rod 200. The torque rather has the result that the body 300 is rotated about the fastening rod 200. This has the consequence that the rod 400 is moved out of the tip V of the recess 310 and now contacts the surface 320 or 330 of the recess 310—depending on the direction of rotation. This state is shown in FIG. 4.

The surfaces 320 and 330 can be curved such that the rod always contacts the surface 320 or 330 over its total length in which it is received in the recess 300. In this case, the contact between the rod 400 and the surface 320 or 300 respectively is linear, independently of the angle of rotation, due to the cylindrical shape of the rod 400.

Shapes of the rod differing from a cylindrical shape are also covered by the invention.

Due to the fact that the two slanted surfaces 320, 330 extend upwardly toward one another and that the rod 400 is arranged in a fixed position, the body 300 and thus also the total heating pan 130 is moved upwardly due to the rotary movement of the heating pan 130.

There is in this respect a contact between the heating pan 130 and a part of the upper side of the machine housing 120. This part serves as an abutment which prevents a further rotation of the heating pan 130 and leads the torque off into the machine housing 120.

It is also conceivable, instead of the arrangement shown in FIGS. 3 and 4, to arrange the body 300 at the fastening rod 200 and to arrange the rod 400 at the heating pan 130. In this case, the open side of the recess 130 faces upwardly in the body 300.

The arrangement in accordance with FIGS. 2 to 4 is active on a torque or on a rotation about the y axis (cf. FIG. 1), i.e. on a rotation about the fastening rod 200. Since the heating pan 130 is to this extent decoupled from the fastening rod 200, the fastening rod 200 does not follow the rotary movement of the heating pan and also is not subject to any torque or is only subject to a small torque. The weighing cell is consequently also not acted on by a torque or is only acted on by a small torque.

Figure 5:
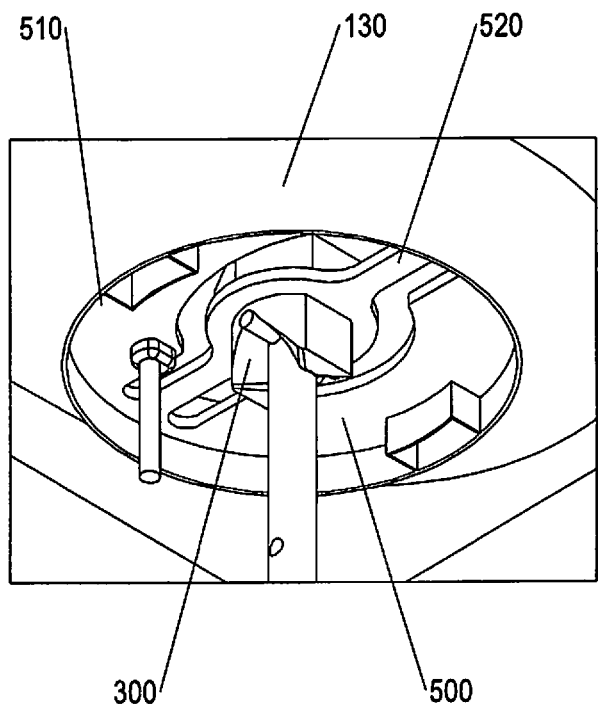
FIG. 5: a further perspective view of the weighing pan from below with a torsion spring.

A second torque limiting device of the peritoneal dialysis machine can be seen from FIG. 5 which prevents an unduly high torque from acting on the weighing cell when a torque about the x axis acts on the heating pan in accordance with FIG. 1. This can be the case, for example, when the heating pan is unevenly loaded with heating bags.

Figure 6:
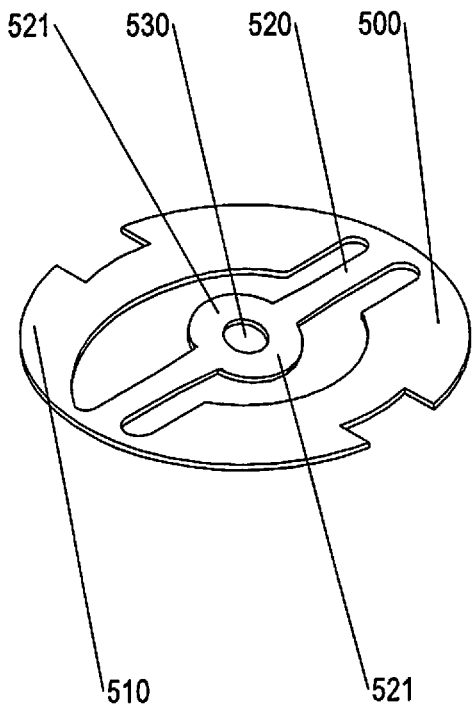
FIG. 6: a perspective view of the torsion spring with a torque action.

As can be seen from FIG. 5, the second torque limiting device comprises a plate-shaped torsion spring 500 which is located on the lower side of the heating pan 130. The torsion spring 500 as such is shown in FIG. 6.

The torsion spring 500 has an outer ring 510 of which two oppositely disposed sides are connected to one another by a web 520. An opening 530 is located in the web 520, said opening being surrounded by a part-circular parts 521 of the web and through which the body 300 of the first torque limiting device extends.

This can be seen from FIG. 5, for example.

If now a torque acts about the axis formed by the web 520 and which corresponds to the x axis in FIG. 1, the central section of the web 520 and the region 521 of the web 520 surrounding the opening 530 is subjected to torsion and bent by the body 300 extending through the opening 530.

The fastening rod 200 and the weighing cell connected thereto do not, however, experience any torque on this tilt movement of the heating pan 130.

The bending of this region results in an inclination of the heating pan 130 overall. As soon as the heating pan 130 contacts a part of the housing, a further bending or a further tilting of the heating pan 130 is prevented and the torque is led off into the machine housing. The weighing cell is thus not only protected from a torque on a rotation about the axis of the fastening rod 200, but also from a torque which occurs on a rotation or on a tiling of the heating pan.

Exemplary bag sizes which are received on the heating pan amount to (width×length×height, each in cm): 29×28×8 with 5 liter bags or 29×31×10 with 6 liter bags or 42×43×4.5 with 5 liter bags or 42×46×4.5 with 6 liter bags with respect to the last bag 17×30×7 as a 2.5 liter bag.

Other bag sizes (volumes and/or dimensions) or multi-chamber bags are also conceivable and covered by the invention.

Each of the four different bag sizes or bag arrangements produce, together with the last bag, the following torques on a support offset from the support point of the heating pan, i.e. from the point at which the fastening rod engages at the heating pan, said torques resulting from the fact that the center of gravity of the loaded heating pan does not coincide with the support point of the heating pan or with the location of the heating cell:

5 liter bag 29×28×8 and last bag with an offset of 20 mm toward the right: 140 N×0.02 m=2.8 Nm 6 liter bag 29×31×10 and last bag with an offset of 15 mm toward the right: 160 N×0.015 m=2.4 Nm 5 liter bag 42×43×4.5 and last bag with an offset of 31 mm toward the left: 140 N×0.031 m=4.3 Nm 6 liter bag 42×46×4.5 and last bag with an offset of 44 mm toward the left: 160 N×0.044 m=7.0 Nm The stiffness of the torsion disk or torsion spring has to be so large that under these loads no inclination of the heating pan occurs which is so large that said heating pan contacts the housing since otherwise no reliable measurement of the weight is possible. The safety factor between the maximum load to be expected and a load which produces a contact of the heating pan on the housing can lie in the region between 2 and 3, such as at 2.5.

It is possible by the present invention, on the one hand, to achieve an exact weighing of the heating pan or of the solution bags located thereon and, on the other hand, reliably to prevent damage to the weighing cell by loads or torques which are too large.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A peritoneal dialysis machine comprising:
a machine housing and having a weighing pan for receiving one or more solution bags, the weighing pan being connected to a weighing cell for weight measurement;
at least one torque limiting device which prevents an occurrence of a torque or of a torque exceeding a limit value in the weighing cell, with the torque limiting device being configured such that, with a torque acting on the weighing pan, it moves the weighing pan such that it comes into contact with the machine housing or with an element connected to the machine housing such that the torque is led off into the machine housing or into the element;
said torque limiting device having a first element and a second element, said first element being formed by a body which has a recess of which at least one surface extends at an inclination with respect to the horizontal and with respect to the vertical, said second element being received in the recess, with the first element being rotatable relative to the second element; and
said torque limiting device including a torsion spring that has a first section which is connected to the weighing pan or to a body arranged at the weighing pan and is subjected to torsion on a tilt movement of the weighing pan.

2. The peritoneal dialysis machine in accordance with claim 1, wherein the torque limiting device is configured such that it only moves the weighing pan at a torque acting on the weighing pan and exceeding a limit value such that it comes into contact with the machine housing or with an element connected to the machine housing such that the torque is led off into the machine housing or into the element.

3. The peritoneal dialysis machine in accordance with claim 1, wherein the recess has two of the inclined surfaces which run toward one another.

4. The peritoneal dialysis machine in accordance with claim 3, wherein the two inclined surfaces form, in the plan view of the first element, the sides of a triangle whose one side is open for the introduction of the second element.

5. The peritoneal dialysis machine in accordance with claim 1, wherein the second element is designed as a rod-shaped part which is preferably cylindrical.

6. The peritoneal dialysis machine in accordance with claim 1, wherein the first element or second element is arranged rotationally fixedly relative to the weighing pan; and in that the other element is arranged rotationally fixedly relative to the machine housing.

7. The peritoneal dialysis machine in accordance with claim 1, wherein the torque limiting device is configured such that it prevent or limits the occurrence of a torque at the weighing cell when the weighing cell is rotated about its fastening axis, with provision preferably being made that the fastening axis extends vertically.

8. The peritoneal dialysis machine in accordance with claim 1, wherein the torsion spring is of plate shape.

9. The peritoneal dialysis machine in accordance with claim 1, wherein the body arranged at the weighing pan is the body that forms the first element.

10. The peritoneal dialysis machine in accordance with claim 9, wherein the first section is arranged at the center of the torsion spring and is surrounded over its full periphery or partially by a second section of the torsion spring.

11. The peritoneal dialysis machine in accordance with claim 1, wherein the torsion spring is arranged at the lower side of the weighing pan.

12. The peritoneal dialysis machine in accordance with claim 1, wherein the torque limiting device is configured such that it limits the torque acting on the weighing cell or prevents the action of a torque on the weighing cell when the weighing cell experiences a tilt movement.

13. The peritoneal dialysis machine in accordance with claim 1, wherein the weighing pan is a heated pan.

14. The peritoneal dialysis machine in accordance with claim 13, wherein a plurality of solution bags containing fresh dialyzate are arranged in the weighing cell.

* * * * *